US00PP32673P2

(12) United States Plant Patent
Hofmann

(10) Patent No.: US PP32,673 P2
(45) Date of Patent: Dec. 22, 2020

(54) ***LOBULARIA* PLANT NAMED 'INLBUMOKNI'**

(50) Latin Name: *Lobularia maritima*
Varietal Denomination: Inlbumokni

(71) Applicant: Birgit Hofmann, Rudesheim am Rhein (DE)

(72) Inventor: Birgit Hofmann, Rudesheim am Rhein (DE)

(73) Assignee: INNOVAPLANT ZIERPLANZIEN GmbH + Co. KG, Gensingen (DE)

( * ) Notice: Subject to any disclaimer, the term of this patent is extended or adjusted under 35 U.S.C. 154(b) by 0 days.

(21) Appl. No.: 16/873,417

(22) Filed: Apr. 9, 2020

(51) Int. Cl.
*A01H 6/20* (2018.01)
*A01H 5/02* (2018.01)

(52) U.S. Cl.
USPC ..... Plt./263.1

(58) Field of Classification Search
USPC ..... Plt./389
See application file for complete search history.

*Primary Examiner* — Annette H Para
(74) *Attorney, Agent, or Firm* — C. A. Whealy

(57) ABSTRACT

A new and distinct cultivar of *Lobularia* plant named 'Inlbumokni', characterized by its compact, outwardly spreading, mounding to trailing plant habit; freely branching habit; freely and continuous flowering habit; relatively long flowering period; light yellow-colored flowers; and good garden performance.

2 Drawing Sheets

Figure 1:
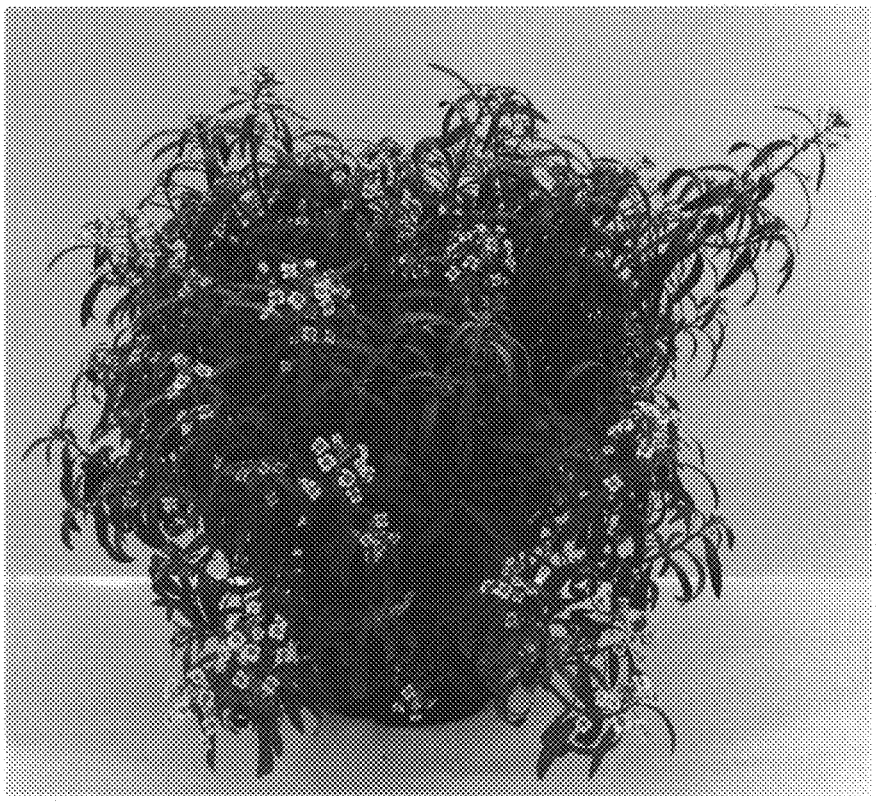

Botanical designation: *Lobularia maritima.*
Cultivar denomination: 'INLBUMOKNI'.

BACKGROUND OF THE INVENTION

The present invention relates to a new and distinct cultivar of *Lobularia* plant, botanically known as *Lobularia maritima* and hereinafter referred to by the name 'Inlbumokni'.

The new *Lobularia* plant is a product of a planned breeding program conducted by the Inventor in Heidesheim, Germany. The objective of the breeding program was to develop new compact and trailing *Lobularia* plants with numerous sterile flowers and long flowering period.

The new *Lobularia* plant originated from a cross-pollination conducted by the Inventor during the summer of 2014 in Heidesheim, Germany of a proprietary selection of *Lobularia maritima* identified as code number Lo13-4002-21, not patented, as the female, or seed, parent, with a proprietary selection of *Lobularia maritima* identified as code number Lo13-4000-2, not patented, as the male, or pollen, parent. The new *Lobularia* plant was discovered and selected by the Inventor as a single flowering plant within the progeny of the stated cross-pollination in a controlled greenhouse environment in Heidesheim, Germany in May, 2015. Asexual reproduction of the new *Lobularia* plant by vegetative terminal cuttings in a controlled greenhouse environment in Heidesheim, Germany since June, 2015 has shown that the unique features of this new *Lobularia* plant are stable and reproduced true to type in successive generations.

SUMMARY OF THE INVENTION

Plants of the new *Lobularia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inlbumokni'. These characteristics in combination distinguish 'Inlbumokni' as a new and distinct *Lobularia* plant:

1. Compact, outwardly spreading, mounding to trailing plant habit.
2. Freely branching habit.
3. Freely and continuous flowering habit.
4. Relatively long flowering period.
5. Light yellow-colored flowers.
6. Good garden performance.

Plants of the new *Lobularia* differ from plants of the female parent selection in the following characteristics:

1. Plants of the new *Lobularia* are more freely branching and denser than and not as open as plants of the female parent selection.
2. Plants of the new *Lobularia* have larger flowers than plants of the female parent selection.
3. Flowers of plants of the new *Lobularia* are more yellow in color than flowers of plants of the female parent selection.

Plants of the new *Lobularia* differ from plants of the male parent selection in the following characteristics:

1. Plants of the new *Lobularia* are denser and more uniform than plants of the male parent selection.
2. Plants of the new *Lobularia* have slightly smaller flowers than plants of the male parent selection.
3. Flowers of plants of the new *Lobularia* are light yellow in color whereas flowers of plants of the male parent selection are white in color.

Plants of the new *Lobularia* can be compared to *Lobularia maritima* 'DLOBU20', disclosed in U.S. Plant Pat. No. 25,142. In side-by-side comparisons, plants of the new *Lobularia* differ from plants of 'DLOBU20' in the following characteristics:

1. Plants of the new *Lobularia* are more vigorous than plants of 'DLOBU20'.

2. Plants of the new *Lobularia* are more trailing than plants of 'DLOBU20'.

BRIEF DESCRIPTION OF THE PHOTOGRAPHS

The accompanying colored photographs illustrate the overall appearance of the new *Lobularia* plant showing the colors as true as it is reasonably possible to obtain in colored reproductions of this type. Colors in the photographs may differ slightly from the color values cited in the detailed botanical description which accurately describe the colors of the new *Lobularia* plant.

The photograph on the first sheet (FIG. 1 of 2) is a side perspective view of a typical flowering plant of 'Inlbumokni' grown in a container.

Figure 2:
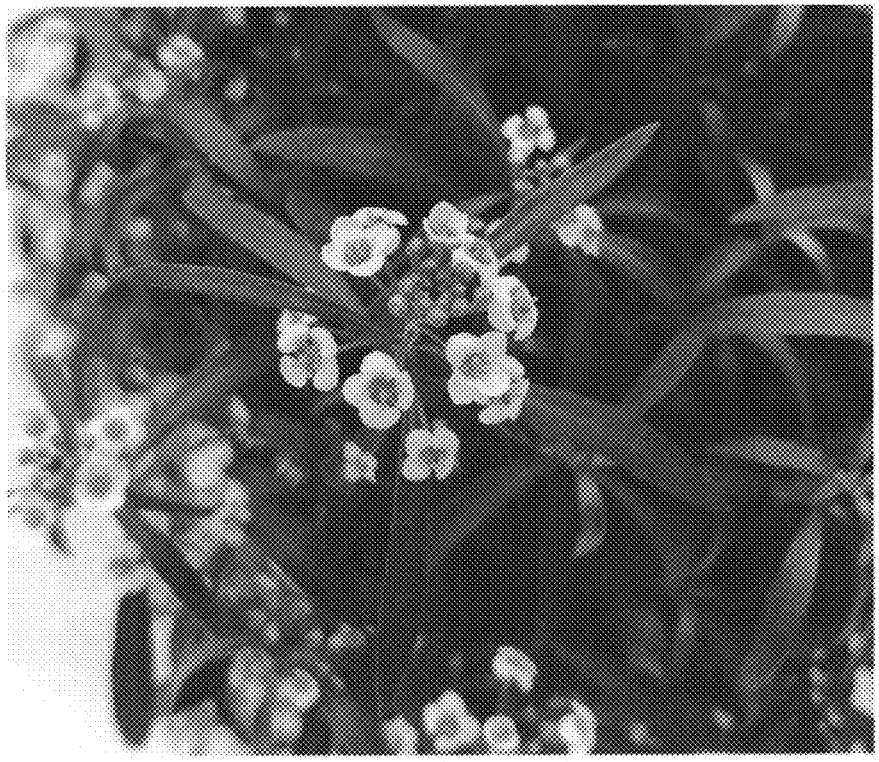

The photograph on the second sheet (FIG. 2 of 2) is a close-up view of a typical flowering plant of 'Inlbumokni'.

DETAILED BOTANICAL DESCRIPTION

The aforementioned photographs and following observations and measurements describe plants grown during the autumn and winter in 10.8-cm containers in a glass-covered greenhouse in Loudon, N.H. and under cultural practices typical of commercial *Begonia* production. During the production of the plants, average daily temperatures ranged from 19° C. to 21° C. Plants were grown under long day/short night conditions and were pinched three weeks after planting. Plants were 14 weeks from planting when the photographs and description were taken. In the following description, color references are made to The Royal Horticultural Society Colour Chart, 2015 Edition, except were general terms of ordinary dictionary significance are used. Measurements were taken on individual plants.

Botanical classification: *Lobularia maritima* 'Inlbumokni'.

Parentage:

*Female, or seed, parent*.—Proprietary selection of *Lobularia maritima* identified as code number Lo13-4002-21, not patented.

*Male, or pollen, parent*.—Proprietary selection of *Lobularia maritima* identified as code number Lo13-4000-02, not patented.

Propagation:

*Type*.—Terminal vegetative cuttings.

*Time to initiate roots, summer*.—About eight days at temperatures about 23° C. to 26° C.

*Time to initiate roots, winter*.—About ten days at temperatures about 18° C. to 22° C.

*Time to produce a rooted young plant, summer*.—About two weeks at temperatures about 23° C. to 26° C.

*Time to produce a rooted young plant, winter*.—About three weeks at temperatures about 18° C. to 22° C.

*Root description*.—Medium in thickness, fibrous; white in color.

*Rooting habit*.—Freely branching; medium density.

Plant description:

*Plant form and growth habit*.—Compact, outwardly spreading, mounding and trailing plant habit; freely branching habit with about lateral branches potentially developing at every node; dense and bushy appearance; moderately vigorous growth habit and moderate to rapid growth rate.

*Plant height*.—About 16 cm.

*Plant diameter* (*area of spread*).—About 36 cm.

*Lateral branches*.—Length: About 21.5 cm. Diameter: About 2.5 mm. Internode length: About 1.25 cm to 1.75 cm. Strength: Strong, flexible. Aspect: Upright to outwardly to eventually trailing. Texture and luster: Fine pubescence; longitudinally ridged; slightly glossy. Color: Close to 144A.

Leaf description:

*Arrangement*.—Alternate; simple; sessile.

*Length*.—About 5.25 cm to 5.75 cm.

*Width*.—About 7.5 mm to 9 mm.

*Shape*.—When developing, linear and becoming narrowly oblanceolate with development; reflexing and twisting.

*Apex*.—Acute to acuminate.

*Base*.—Cuneate to attenuate.

*Margin*.—Entire, not undulate.

*Texture and luster, upper and lower surfaces*.—Fine pubescence; slightly glossy.

*Venation pattern*.—Single midvein discernible.

*Color*.—Developing and fully developed leaves, upper surface: Close to 147A; close to 147A. Developing and fully developed leaves, lower surface: Close to 147B; venation, close to 147B.

Flower description:

*Flower type and habit*.—Single rotate flowers arranged singly or in axillary and terminal cymes; flowers face initially upright and mostly outwardly with inflorescence development; freely flowering habit, about 20 flowers per inflorescence.

*Natural flowering season*.—Relatively long flowering period; plants flower continuously from spring until autumn in Germany.

*Flower longevity on the plant*.—About five to seven days; flowers persistent.

*Fragrance*.—Faintly fragrant; sweet, vanilla-like.

*Inflorescence height*.—About 8.5 cm.

*Inflorescence diameter*.—About 7.5 cm.

*Flower diameter*.—About 5 mm to 6 mm.

*Flower depth* (*height*).—About 3 mm.

*Flower buds*.—Length: About 2 mm. Diameter: About 1 mm. Shape: Roughly spherical to ovoid. Texture and luster: Smooth, glabrous; matte. Color: Close to 144A.

*Petals*.—Quantity and arrangement: Four petals arranged in a single whorl. Length: About 3 mm. Width: About 3 mm. Shape: Spatulate; reflexing. Apex: Obtuse. Base: Truncate with a short stalk. Margin: Entire, not undulate. Texture and luster, upper and lower surfaces: Smooth, glabrous; matte. Color: When opening, upper and lower surfaces: Close to NN155C to NN155D. Fully opened, upper and lower surfaces: Close to NN155A; venation, close to NN155A; color becoming closer to 11D with subsequent development.

*Sepals*.—Quantity and arrangement: Four sepals arranged in a single whorl; calyx, star-shaped. Length: About 1.5 mm. Width: About 1 mm. Shape: Lanceolate. Apex: Acute to acuminate. Base: Truncate, not stalked. Margin: Entire. Texture and luster, upper and lower surfaces: Smooth, glabrous; matte. Color, upper surface: Close to 144A. Color, lower surface: Close to 144A to 144B.

*Peduncles*.—Length: About 2.5 cm to 3.25 cm. Width: About 2 mm. Strength: Strong, wiry and flexible. Aspect: About 45° from stem axis. Texture and luster: Fine and sparse pubescence; longitudinally ridged; moderately glossy. Color: Close to 144A.

*Pedicels*.—Length: About 1 cm to 1.5 cm. Width: About 1 mm. Strength: Strong, wiry and flexible. Aspect: Initially upright to almost horizontal and arching. Texture and luster: Fine and sparse pubescence; longitudinally ridged; moderately glossy. Color: Close to between 144A and 146A.

*Reproductive organs*.—Stamens: Quantity per flower: Four. Filament length: About 1.5 mm to 2 mm. Filament color: Close to 144A to 144B. Anther shape: Oblong. Anther size: About 0.5 mm by 1 mm. Anther color: Close to 9A. Pollen amount: None observed. Pistils: Quantity per flower: One. Pistil length: About 2.5 mm to 3 mm. Style length: About 1.5 mm to 2 mm. Style color: Close to 144A. Stigma shape: Rounded. Stigma color: Close to 154D. Ovary color: Close to 144A.

*Seeds and fruits*.—To date, seed and fruit production have not been observed on plants of the new *Lobularia*.

Pathogen & pest resistance: Plants of the new *Lobularia* have not been noted to be resistant to pathogens or pests common to *Lobularia* plants.

Garden performance: Plants of the new *Lobularia* have been observed to have good garden performance and to tolerate temperatures ranging from about 4° C. to about 35° C.

It is claimed:

1. A new and distinct *Lobularia* plant named 'Inlbumokni' as illustrated and described.

* * * * *